(12) United States Patent
Vega et al.

(10) Patent No.: US 11,989,819 B2
(45) Date of Patent: May 21, 2024

(54) METHOD AND APPARATUS FOR THE VISUALIZATION OF THREE-DIMENSIONAL OBJECTS

(71) Applicant: Siemens Healthcare GmbH, Erlangen (DE)

(72) Inventors: Fernando Vega, Erlangen (DE); Stefan Thesen, Dormitz (DE); Sebastian Budz, Erlangen (DE); Robert Schneider, Rosstal (DE); Sebastian Krueger, Erlangen (DE); Alexander Brost, Erlangen (DE); Volker Schaller, Erlangen (DE); Bjoern Nolte, Fuerth (DE)

(73) Assignee: Siemens Healthineers AG, Forchheim (DE)

( * ) Notice: Subject to any disclaimer, the term of this patent is extended or adjusted under 35 U.S.C. 154(b) by 288 days.

(21) Appl. No.: 17/500,161

(22) Filed: Oct. 13, 2021

(65) Prior Publication Data
US 2022/0122312 A1   Apr. 21, 2022

(30) Foreign Application Priority Data

Oct. 20, 2020   (DE) .................. 10 2020 213 234.8

(51) Int. Cl.
*G06T 15/08*   (2011.01)
*G06F 40/279*  (2020.01)
*G10L 15/22*   (2006.01)

(52) U.S. Cl.
CPC .......... *G06T 15/08* (2013.01); *G06F 40/279* (2020.01); *G10L 15/22* (2013.01); *G06T 2210/41* (2013.01); *G10L 2015/223* (2013.01)

(58) Field of Classification Search
CPC ... G06T 15/08; G06T 2210/41; G06F 40/279; G10L 15/22; G10L 2015/223
See application file for complete search history.

(56) References Cited

U.S. PATENT DOCUMENTS

2005/0168461 A1*  8/2005  Acosta .................. G06T 19/00
                                                     345/419
2017/0178266 A1*  6/2017  Schmidt ................ G06F 40/134
(Continued)

FOREIGN PATENT DOCUMENTS

EP     3178068 B1    9/2018

OTHER PUBLICATIONS

Levoy M. et al.: "Display of Surfaces from Volume Data", IEEE Computer Graphics an Applications, Bd. 8, Nr. 3, 1988, Seiten 29-37; Marc Levoy.
(Continued)

*Primary Examiner* — Michelle Chin
(74) *Attorney, Agent, or Firm* — Harness, Dickey & Pierce, P.L.C.

(57) ABSTRACT

A computer-implemented method and a corresponding apparatus are provided for the provision of a two-dimensional visualization image having a plurality of visualization pixels for the visualization of a three-dimensional object represented by volume data for a user. Context information for the visualization is obtained by the evaluation of natural language and is taken into account in the visualization. The natural language can be in the form of electronic documents, which are assigned or can be assigned to the visualization process. In addition, the natural language can be in the form of a speech input of a user, during or after the visualization.

26 Claims, 5 Drawing Sheets

(56) References Cited

U.S. PATENT DOCUMENTS

2017/0294042 A1 10/2017 Engel
2018/0121468 A1* 5/2018 Setlur .................. G06F 16/248

OTHER PUBLICATIONS

Kajiya et al.:"The rendering equation", ACM SIGGRAPH Computer Graphics, vol. 20, No. 4, Aug. 1986, pp. 143-150).

* cited by examiner

METHOD AND APPARATUS FOR THE VISUALIZATION OF THREE-DIMENSIONAL OBJECTS

PRIORITY STATEMENT

The present application hereby claims priority under 35 U.S.C. § 119 to German patent application number DE 102020213234.8 filed Oct. 20, 2020, the entire contents of which are hereby incorporated herein by reference.

FIELD

Example embodiments of the invention generally lie in the field of volume rendering, in other words the representation or visualization of three-dimensional bodies or objects.

BACKGROUND

The modeling, reconstruction or visualization of three-dimensional objects has a wide range of application in the fields of medicine (for example CT, PET), physics (for example electron structure of large molecules) or geophysics (composition and position of layers of earth). Typically, the object to be examined is irradiated (for example by way of electromagnetic waves or soundwaves) in order to examine its composition. The scattered radiation is detected and properties of the body are determined from the detected values. Conventionally, the result consists in a physical variable (for example density, tissue type, elasticity, speed), whose value is determined for the body. As a rule, a virtual grid is used in this case at whose grid points the value of the variable is determined. These grid points are conventionally referred to as voxels. The term "voxel" is a portmanteau formed from the terms "volume" and "pixel". A voxel corresponds to the spatial coordinate of a grid point, to which the value of a variable at this location is assigned. This is usually a physical variable, which can be represented as a scalar or vectorial field, in other words the corresponding field value is assigned to the spatial coordinate. The value of the variable or of the field at any location (in other words at any object points of the examined object) can be obtained by interpolation of the voxels.

A three-dimensional representation of the examined object or body is generated from the voxels on a two-dimensional display area (for example a screen or a panel or lens of what are known as "augmented reality glasses") for visualization of the volume data. In other words, voxels (defined in three dimensions) are mapped onto pixels (defined in two dimensions) of a two-dimensional visualization image. The pixels of the visualization image will also be called visualization pixels below. The mapping is conventionally referred to as volume rendering. The implementation of the volume rendering determines how information contained in the voxels is rendered by way of the pixels.

One of the most used methods of volume rendering is what is known as ray casting (cf. Levoy: "Display of Surfaces from Volume Data", IEEE computer Graphics and Applications, issue 8, no. 3, May 1988, pages 29-37). In ray casting, simulated rays, which emanate from the eye of an imaginary observer, are sent through the examined body or the examined object. Along the rays, RGBA values are determined from the voxels for sampling points and are combined by way of Alpha Compositing or Alpha Blending to form pixels for a two-dimensional image. In the expression RGBA, the letters R, G and B stand for the color components red, green and blue of which the color contribution of the corresponding sampling point is composed. A stands for the ALPHA value, which is a measure of the transparency at the sampling point. The respective transparency is used in the overlaying of RGB values at sampling points relative to the pixel. Lighting effects are conventionally taken into account by way of a lighting model in the context of a method designated "Shading".

A further method of volume rendering is what is known as path tracing (cf. Kajiya: "The rendering equation", ACM SIGGRAPH computer Graphics, issue 20, no. 4, August 1986, pages 143-150). In this case, a plurality of simulated rays are shot into the volume data per visualization pixel, and these then interact with the volume, in other words are reflected, refracted or absorbed, wherein every time (apart from in the case of absorption) at least one random ray is generated. Each simulated ray thus looks for its path through the volume data. The more virtual rays used per visualization pixel, the more the ideal image is approached. In particular the processes and methods described in EP 3 178 068 B1 can be applied here. The disclosure of EP 3 178 068 B1 is hereby incorporated herein, in its entirety, by way of reference.

Users primarily in the medical and clinical sector can be effectively supported by visualization methods of this kind since a representation of this kind allows a rapid overview of complex anatomical relationships. For example, this allows for better planning of surgical interventions. Furthermore, such visualization images enable the creation of meaningful medical reports.

SUMMARY

The inventors have discovered that a primary technical obstacle in implementation of a system for interactive volume rendering is the complex operation of such systems. In order to generate a visualization image optimally adjusted to the situation, many parameters of such a system have to be set and optimized. For example, particular anatomies are highly relevant to different medical issues, while other anatomies are irrelevant and obstruct the view of what is essential.

The inventors have discovered that a large number of parameters has to be purposefully adjusted in the case of volume rendering algorithms in order to work out such aspects. Thus, for example, particular anatomies can be represented transparently while other anatomies can be optimally illuminated. In order to make suitable adjustments, a user requires a certain amount of time, which is often not available in daily clinical practice, in addition to some background knowledge in respect of the mode of operation of the respective volume rendering algorithm. What is more, the inventors have discovered that adversely selected visualization parameters can obstruct pathologically relevant issues and lead to incorrect decisions.

It is an aim of at least one embodiment of the present invention, therefore to provide methods and apparatuses for the visualization of volume data that are improved in this respect. In at least one embodiment, this should address the problem of providing visualizations, which are better adapted to the underlying problem and, moreover, can be adapted by a user in as simple and intuitively operable a manner as possible.

At least one embodiment of the invention is directed to a method, an apparatus, a computer program product or a computer-readable storage medium. Advantageous developments are disclosed in the claims.

The inventive solution of embodiments will be described below in relation to the apparatuses as well as in relation to the method. Features, advantages or alternative embodiments mentioned in this connection should likewise also be transferred to the other subject matters, and vice versa. In other words, the concrete claims (which are directed, for example, to a device) can also be developed with the features, which are described or claimed in connection with a method. The corresponding functional features of the method are formed by corresponding concrete modules.

Furthermore, embodiments will be described in relation to methods and apparatuses for the visualization of a three-dimensional body as well as in relation to methods and apparatuses for adjusting trained functions. Features and alternative embodiments of data structures and/or functions in methods and apparatuses for determination can be transferred here to analogous data structures and/or functions in methods and apparatuses for adjusting. Analogous data structures can be identified here in particular by the use of the prefix "training". Furthermore, the trained functions used in methods and apparatuses for the visualization of a three-dimensional body can have been adjusted and/or provided in particular by methods and apparatuses for adjusting trained functions.

According to at least one embodiment, a computer-implemented method for the provision of a two-dimensional visualization image having a plurality of visualization pixels for the visualization of a three-dimensional object represented by volume data is provided for a user. The method comprises:
  providing context data containing natural language and/or text in respect of the visualization of the three-dimensional object;
  determining a mapping indication based on the context data, wherein the mapping indication has information about a mapping of the volume data onto the visualization image that is suitable based on the context data;
  determining a mapping rule based on the mapping indication;
  mapping the volume data onto the visualization pixels using the mapping rule for the creation of the visualization image; and
  providing the visualization image.

According to a further embodiment, a computer-implemented method for providing a trained function for determining a mapping rule is disclosed. The method comprises:
  providing training input data, wherein the training input data has context data containing natural language and/or text in respect of the visualization of a three-dimensional object and volume data representing the three-dimensional object;
  providing training output data, wherein the training output data has a mapping rule for the generation of a suitable two-dimensional visualization image by mapping the volume data;
  generating a training mapping rule by applying the trained function to the training input data;
  comparing the training mapping rule with the training output data;
  adjusting the trained function based upon the comparison.

According to a further embodiment, an apparatus is disclosed for the provision of a two-dimensional visualization image having a plurality of visualization pixels for visualization of a three-dimensional object represented by volume data for a user, which apparatus comprises:
  an interface, which is designed to receive the volume data and context data containing natural language in respect of the visualization of the three-dimensional object;
  a configuration module, which is designed to:
  determine a mapping indication based on the context data (and optionally on the volume data), wherein the mapping indication comprises information about a mapping of the volume data, which is suitable based on the context data, onto the visualization image; and
  determine a mapping rule based on the mapping indication; and
  a visualization module, which is designed to:
  map the volume data onto the visualization pixels using the mapping rule for the creation of the visualization image; and
  provide the visualization image.

The configuration module and/or the visualization module of an embodiment can be part of an computing facility. The configuration module can be designed to carry out the configuration algorithm. The visualization module can be designed to carry out the image synthesis algorithm.

The computing facility can be designed as a central or decentral computing facility. The computing facility can have one or more processor(s). The processors can be designed as a central processing unit (CPU for short) and/or as graphics processing unit (GPU for short). The computing facility can be designed as what is known as a system-on-a-chip (SoP for short), which controls all functions of a device. Alternatively, the computing facility can be implemented as a local or Cloud-based processing server.

The invention relates in a further embodiment to a computer program product, which comprises a program and can be loaded directly into a storage device of a programmable computing facility and has program code/segments, for example libraries and auxiliary functions, in order to carry out an embodiment of a method for the visualization of a three-dimensional object in particular according to the embodiment when the computer program product is run.

Furthermore, the invention relates in a further embodiment to a computer program product, which comprises a program and direct can be loaded directly into a storage device of a programmable computing facility and has program code/segments, for example libraries and auxiliary functions, in order to carry out a method for the provision of a trained function in particular according to the embodiment when the computer program product is run.

The computer program products of an embodiment can comprise software with a source code, which still has to be compiled and linked or which only has to be interpreted, or an executable software code, which for execution only has to be loaded into the processing unit. As a result of the computer program products the method can be carried out quickly, repeatedly in an identical manner and robustly. The computer program products are configured such that they can carry out the inventive method steps by way of the computing facility. The computing facility has to have in each case the requirements such as an appropriate main memory, an appropriate processor, an appropriate graphics card or an appropriate logic unit, so the respective method steps of an embodiment can be efficiently carried out.

The computer program products are stored, for example in an embodiment, on a computer-readable storage medium or saved on a network or server from where they can be loaded into the processor of the respective computing facility, which is directly connected to the computing facility or can be designed as part of the computing facility. Furthermore, control information of the computer program products can be stored on a computer-readable storage medium. The control information of the computer-readable storage medium can be configured in such a way that it carries out an inventive method when the data carrier is used in an computing facility. Examples of computer-readable storage medium are a DVD, a magnetic tape or a USB stick on which electronically readable control information, in particular software, is stored. When this control information is read from the data carrier and stored in an computing facility, all inventive embodiments of the previously described method can be carried out. The invention can thus also start from the computer-readable medium and/or the computer-readable storage medium. The advantages of the proposed computer program product or the associated computer-readable media substantially match the advantages of an embodiment of the proposed method.

At least one embodiment of the invention is directed to a computer-implemented method for creating a two-dimensional visualization image including a plurality of visualization pixels for visualization of a three-dimensional object represented by volume data for a user, the method comprising:

providing context data containing at least one of natural language and text for the visualization of the three-dimensional object;

determining a mapping rule based on the volume data and the context data; and mapping the volume data onto the plurality of visualization pixels using the mapping rule, for creation of the two-dimensional visualization image.

At least one embodiment of the invention is directed to an apparatus for providing a two-dimensional visualization image including a plurality of visualization pixels for visualization of a three-dimensional object represented by volume data for a user, comprising:

an interface, designed to receive the volume data and at least one of natural language and context data containing text relating to the visualization of the three-dimensional object;

a computing facility, designed to determine a mapping rule based on the volume data and the context data; and a visualization module, designed to
  map the volume data onto the plurality of visualization pixels using the mapping rule, to create the two-dimensional visualization image; and
  provide the visualization image.

At least one embodiment of the invention is directed to a non-transitory computer program product storing a computer program, directly loadable into a storage device of a computing facility, including program segments to carry out the method of an embodiment when the program segments are run in the computing facility.

At least one embodiment of the invention is directed to a non-transitory computer-readable storage medium storing program segments, readable and runnable by a computing facility, to carry out the method of an embodiment when the program segments are run in the computing facility.

At least one embodiment of the invention is directed to an apparatus for providing a two-dimensional visualization image including a plurality of visualization pixels for visualization of a three-dimensional object represented by volume data for a user, comprising:

an interface to receive the volume data and at least one of natural language and context data containing text relating to the visualization of the three-dimensional object;

at least one processor to determine a mapping rule based on the volume data and the context data to map the volume data onto the plurality of visualization pixels using the mapping rule, to create the two-dimensional visualization image.

At least one embodiment of the invention is directed to an apparatus further comprising a display to display the two-dimensional visualization image.

BRIEF DESCRIPTION OF THE DRAWINGS

Further particulars and advantages of the invention will become obvious from the following explanations of example embodiments with reference to schematic drawings. Modifications mentioned in this connection can be combined with one another in each case in order to form new embodiments. Identical reference numerals will be used in different figures for identical features.

In the drawings.

DETAILED DESCRIPTION OF THE EXAMPLE EMBODIMENTS

Figure 1:
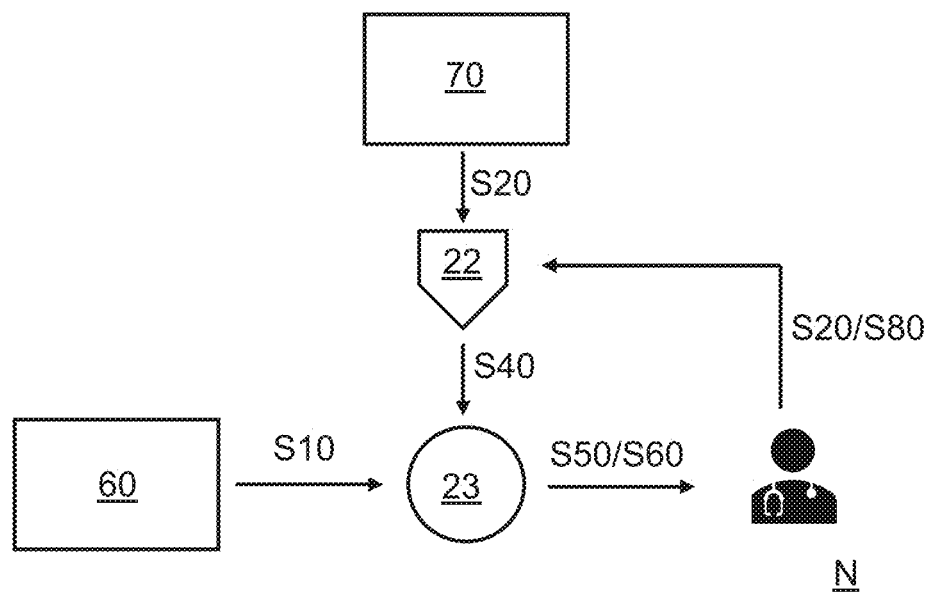
FIG. 1 shows a schematic representation of a first embodiment of a system/method for the visualization of a three-dimensional object.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment, a computer-implemented method for the provision of a two-dimensional visualization image having a plurality of visualization pixels for the visualization of a three-dimensional object represented by volume data is provided for a user. The method comprises:

providing context data containing natural language and/or text in respect of the visualization of the three-dimensional object;

determining a mapping indication based on the context data, wherein the mapping indication has information about a mapping of the volume data onto the visualization image that is suitable based on the context data;

determining a mapping rule based on the mapping indication;

mapping the volume data onto the visualization pixels using the mapping rule for the creation of the visualization image; and providing the visualization image.

It is an idea of at least one embodiment of the present invention, during the creation of visualization images, in particular by way of a volume rendering method, to evaluate available context data in respect of the visualization, with this context data containing information, which is in the form of natural language. The context data can reflect the problem underlying the visualization. The visualization can be better adjusted to the underlying problem by incorporating the context data in the visualization pipeline. Since, according to one aspect, the context data can comprise, in particular, speech inputs of the user, a possibility is thus opened up for intuitively influencing the visualization, and, more precisely, without it being necessary for the user to have deeper knowledge about the process of volume rendering as such.

In other words, at least one embodiment of a computer-implemented method is provided for the provision of a two-dimensional visualization image having a plurality of visualization pixels for the visualization of a three-dimensional object represented by volume data for a user. Context information for the visualization is obtained in the process by the evaluation of natural language and is taken into account in the visualization. The natural language can be in the form of electronic documents, which are or can be assigned to the visualization process. In addition, the natural language can be in the form of a speech input of a user relating to the visualization, which speech input can be made before, during or after the visualization.

The user can be, in particular, the recipient of the visualization and therewith that person for who the visualization was created. The user can be, in particular, a doctor or a patient.

The volume data can contain a plurality of voxels. A voxel ("volume pixel" or three-dimensional pixel) is a volume element, which represents a value on a regular grid in the three-dimensional space. Voxels are analogous to pixels, which represent two-dimensional image data. As with pixels, the voxels themselves typically do not contain their position in the space (their coordinates), instead their coordinates are derived based upon their positions relative to other voxels (their positions in the data structure, therefore, which forms a single volume image). The value of a voxel can represent different physical properties of the three-dimensional object, such as a local density. In computed tomography scans (CT scans), the values are expressed, for example, in Hounsfield units, which represent the opacity of a mapped material in respect of X-rays. The volume data thereby describes a three-dimensional object in an object volume. In particular, the volume data can disclose a (in particular inhomogeneous) density of the three-dimensional object in the object volume.

The volume data can be, in particular, medical image data of a patient. The volume data can be provided, in particular, by a medical imaging method. The imaging methods can be based, for example, on radioscopy, computed tomography (CT), magnetic resonance tomography (MR), ultrasound and/or positron emission tomography (PET). The three-dimensional object can accordingly be a body or body part of a patient. The three-dimensional object can comprise one or more organ(s) of the patient.

The volume data can be mapped using an image synthesis algorithm. The image synthesis algorithm can be understood, in particular, as a computer program product, which is designed for mapping the volume data onto a two-dimensional projection area or for volume rendering of the three-dimensional body. The projection area is given by the visualization image. The image synthesis algorithm can have program components in the form of one or more instruction(s) for a processor for calculation of the visualization image. The visualization image is composed of a plurality of visualization pixels. The resolution of the visualization image in respect of the visualization pixels can be, in particular, spatially constant or homogeneous or spatially uniform. Other terms for image synthesis algorithms are, for example, "renderer", "render algorithm" or "volume renderer". The image synthesis algorithm can be provided, for example, in that it is held available in a storage facility or is loaded into a main memory of a suitable data processing facility or is provided generally for application.

The image synthesis algorithm can implement different methods for the visualization of a volume data set individually or in combination. For example, the image synthesis algorithm can have a ray casting module and/or a path tracing module.

Providing the volume data can comprise, for example, holding available and/or retrieving the volume data in or from a storage facility and/or loading the volume data, for example into a main memory of a suitable data processing facility, or generally making it available for an application or a use. A plurality of different volume data can exist or be provided for a patient in this case.

Providing the context data can comprise, for example, holding available and/or retrieving the context data in or from a storage facility and/or loading the volume data, for example into a main memory of a suitable data processing facility, or generally making it available for an application or use. The natural language can comprise, for example, text or spoken word.

Context data in respect of the visualization can refer to information relevant to the visualization. It can indicate, for example, which perspectives, transfer functions, or which partial objects of the object to be visualized are particularly relevant to the visualization. For example, the context data can literally disclose which partial object, or in the case of medical volume data, which organ, is particularly relevant to the visualization. If a medical report (as a form of context data) contains, for example, statements on the liver of the patient, it is possible to conclude that this organ should primarily be displayed in the visualization. Information of this kind is referred to as a mapping indication.

The mapping indication is converted into a mapping rule, which can be understood, in particular, as an instruction as to how the mapping indication can be suitably implemented in the context of a visualization. Returning to the above example, for optimum visualization of the liver, an optimum perspective, optimum scene lighting, an optimum coloring can be selected for the mapping of the volume data. In addition, fewer relevant regions of the volume data can be omitted or cut away or represented transparently in the visualization.

According to at least one embodiment, the volume data is mapped by a volume rendering method, in particular using an ray casting method and/or path tracing method.

Particularly realistic visualizations can be generated by methods of this kind, and this increases the benefit of the method. The methods are complex in application but the inventive consideration of the context data means the methods can be easily operated and automatically provide an optimum visualization.

According to at least one embodiment, determining the mapping rule comprises one or more of the following step(s):

establishing a suitable perspective;
establishing a suitable scene illumination;
establishing a suitable transfer function;
establishing a suitable transparency of one or more region(s) of the volume data;
establishing a suitable cutting plane through the volume data;
establishing a suitable region of interest inside the volume data; and/or
establishing one or more suitable item(s) of additional information for overlaying in the visualization image.

The visualization can consequently be optimally adjusted to the context data.

Transfer functions often comprise representation parameters. Representation parameters are often very complex. They assign to each gray value in the three-dimensional volume a particular color, transparency, contrast, illumination, definition and the like. In general terms, the representation parameters influence the type of representation of objects of the corresponding object type in the visualization image output to the user.

According to a further implementation of at least one embodiment, the method can also comprise:

determining, based on the mapping indication, a sequence of individual visualization images to be created,
determining a mapping rule in each case for the individual visualization images,
providing the individual visualization images based on the mapping rules,
providing a visualization stream (or a video) based on the individual visualization images.

The user can be automatically offered tracking shots through the volume data to be visualized by the provision of the visualization stream, and this can simplify the perception of specific medical issues, which can be indicated by the context data.

According to one development of at least one embodiment, the method can also comprise:

determining progression parameters for the provision of the individual visualization images based on the mapping indication, wherein the progression parameters are selected from a progression of a perspective, a progression of an enlargement factor, a progression of an arrangement position of a clipping plane and/or a progression of a transparency setting.

In particular, a rotation or the selective observation of organs or of organ systems can thus take place.

According to one implementation of at least one embodiment, the volume data comprises a plurality of different volume data sets of the patient and the method also comprises the following steps:

selection or one or more suitable volume data set(s) from the plurality of provided volume data sets based on the mapping indication, wherein the mapping indication and/or the mapping rule is determined in such a way that the visualization image is generated based upon the selected volume data sets.

In other words, volume data sets for the visualization are purposefully selected for the respective problem based on the available volume data and the context information, and this improves the convenience and the time expenditure for the user.

According to one implementation of at least one embodiment, at least two different volume data sets are selected in the step of selection of one or more suitable volume data set(s), with the mapping indication and/or the mapping rule being determined in such a way that the visualization image is generated based upon the at least two different volume data sets.

Different volume data sets can thus be combined in the creation of a visualization image. Complementary views can be shown in a visualization image thereby.

According to one implementation of at least one embodiment, the at least two different volume data sets comprise a first volume data set and a second volume data set, wherein the first volume data set was generated by a computed tomography scan of an acquisition region (of the patient) with a first radiation spectrum (of a first X-ray energy) and the second volume data set was generated by a computed tomography scan of the acquisition region with a second radiation spectrum (of a second X-ray energy different from the first) different from the first.

Consequently, two scans, which were obtained with different radiation spectra or at different energy levels, are overlaid and evaluated. This allows improved images to be calculated since, for example, artifacts, which are caused by beam hardening, can be compensated.

According to at least one embodiment, the object has a plurality of individual objects, which are mapped in the volume data set. Furthermore, determining the mapping rule comprises the selection of one or more of the individual object(s) for representation in the visualization image. In particular, a separate transfer function, optimized for the respective individual object, can be used for each selected individual object.

According to one further embodiment, determining the mapping rule also comprises adjusting the mapping rule based on the selected one or more individual object(s).

Consequently, a mapping rule suitable for the selected individual objects can be automatically generated, and this eases the workload of the user in having to look for suitable parameters for visualization themselves.

The visualization can thereby be purposefully directed to the individual objects indicated by the context data. In particular, the individual objects can be different organs or anatomies of a patient.

According to one embodiment, the method also comprises the step of determining object information from the context data, with the step of selecting taking place based upon the object information.

The object information can indicate, for example, which of the individual objects are relevant to a visualization. If the context data contains, for example, one or more voice command(s) of the user, which are directed to an individual object (for example the liver of the patient) this can be taken into account accordingly in the visualization. The same applies if the context data comprises, for example, one or more medical report(s), in which one or more individual object(s) are mentioned.

As a result, the object which is relevant can be automatically selected from the context data for the visualization and the visualization parameters can then automatically be adjusted without the user having to act.

According to one embodiment, the method also has the step of recognizing or identifying one or more individual object(s) in the volume data. In particular, a segmentation method and in particular a multi-organ segmentation can be used (or be applied to the volume data). The step of selecting then takes place in particular based upon the one or more individual object(s) recognized in this way.

In a two-stage selection process, it is thereby possible to first of all determine which objects (organs) are even represented in the volume data, whereupon it is then possible to determine by evaluation of the context data which of the represented objects are especially relevant to a visualization.

According to one embodiment, the method also comprises the following step:

acquiring acquisition information from the volume data and/or the context data, wherein the acquisition information contains information about how the volume data was generated; wherein the mapping indication and/or the mapping rule is also determined based upon the acquisition information.

The acquisition information can comprise, for example, information about with which imaging modality the volume data was generated. By way of example, the acquisition information can indicate, for example, that the volume data was generated with a magnetic resonance device, a computed tomography device, an (4D-)ultrasound device, etc. Furthermore, the acquisition information can comprise information about with which imaging protocols the volume data was generated, for example which MR protocol was used, therefore, whether and which contrast medium was administered, whether, for example, an angiography run was carried out, etc.

Taking into account the acquisition information means the mapping indication and/or the mapping rule can be adjusted better and the volume data can be adjusted and the quality of the visualization image can be increased. The acquisition information can be obtained directly from the volume data (because, for example, a particular form of volume data points to a particular imaging modality or this is stored in metadata relating to the volume data) or can be contained in the context data (for example, because a medical report indicates that a particular volume data set was generated with a CT device):

According to one embodiment, the one or more of the individual object(s) is also selected based upon the acquisition information.

Consequently, it is possible to take into account the fact that particular scan modalities and/or scan modes are especially well suited to the representation of certain individual objects and others, in turn, less so. If the acquisition information comprises, for example, information to the extent that an angiography run was carried out, the selection of the vascular tree of the patient as the individual object to be represented is with some certainty expedient.

According to one embodiment, selecting one or more individual object(s) comprises a selection of at least one virtual individual object, which is not contained in the volume data, wherein the mapping indication and/or the mapping rule is determined in such a way that the at least one virtual individual object is represented in the visualization image.

According to some implementations, the at least one virtual individual object can be represented in second volume data different from the volume data. In this connection, the term virtual should be taken to mean "not contained in the volume data". The second volume data can likewise be volume data of the patient. The second volume data can have been acquired in particular with an imaging modality, which is different from an imaging modality with which the volume data was acquired. For example, the volume data can have been acquired with an MR device while the second volume data was acquired with a CT device. Consequently, complementary views may advantageously be combined in one visualization image. According to further implementations, the second volume data can be volume data of a second patient, which differs from the patient. Consequently, comparisons between different patients are made possible. According to further implementations, the virtual individual object can refer to an artificial object such as an implant. The geometric and/or optical properties can be in the form, for example, of separate object data.

According to some implementations, the step of providing the mapping indication and/or the mapping rule comprises registering the at least one virtual individual object with the volume data (or the second volume data with the volume data and/or the object data with the volume data), with the mapping indication and/or the mapping rule being determined based upon the registration.

According to some implementations, the method also comprises selecting the second volume data from a plurality of volume data sets of the patient based on the volume data and/or the context data.

Consequently, second volume data can be purposefully selected for a patient and be used for incorporation of the at least one virtual individual object in the visualization.

According to one embodiment, the method includes receiving one or more speech input(s) of a user, with the context data being provided based upon the speech inputs of the user.

In other words, the visualization can consequently be voice-controlled. The user can indicate by way of a voice command, for example, which partial object or which organ he would willingly like to see. This is inventively automatically converted into a mapping rule. Consequently, especially simple, intuitive operation of the visualization method is possible.

According to one embodiment, the speech input is received after providing the visualization image and the method also has the following steps:

adjusting the mapping rule based on the context data;

mapping the volume data onto the visualization pixels with the image synthesis algorithm using the adjusted mapping rule for the creation of an adjusted visualization image; and provision of the adjusted visualization image.

Consequently, continuous interactive adjustment of the visualization by way of speech input is possible.

According to one embodiment, receiving one or more speech input(s) of the user comprises:

receiving an audio signal containing natural language of the user, a beginning of a speech input of the user in the audio signal, analysis of the speech input of the user in order to identify one or more voice command(s) of the user directed to the visualization of the volume data, and providing the context data based on the one or more voice command(s).

The audio signal can contain, in particular, sound information. The audio signal can be an analog or a digital or digitalized signal. The digitalized signal can be generated starting from the analog signal for example by an analog-to-digital converter. Accordingly, the step of receiving can comprise a step of providing a digitalized audio signal based on the received audio signal or a digitalization of the received audio signal. Receiving the audio signal can comprise, in particular, registering the audio signal by way of a suitable sensor, for example an acoustic sensor such as a microphone.

The audio signal can comprise communication of a user, such as an instruction to be carried out or a question. In other words, the audio signal can comprise a speech input of the operator in natural language. Typically, speech spoken by humans is referred to as natural language. Natural speech can also have an inflection and/or intonation for modulation of the communication. In contrast to formal speech, natural language can have structural and lexical ambiguities.

It can be provided firstly to recognize the beginning of such a speech input in the audio signal. In other words, an activity recognition can be carried out, which shows when the audio signal contains spoken speech. From the instant at which a speech input was recognized, the audio signal is relevant to further analysis in order to infer, for example, the content of the speech input of the user. The recognition of a beginning of a speech input can comprise, in particular, recognition of a human voice in the audio signal. This can occur by way of signal analysis by, for example, values such as frequency, amplitude, modulations, etc. being recognized in the audio signal, which are characteristic of the human voice.

The speech input contained in the audio signal is continuously analyzed from the recognized beginning of the speech input. Accordingly, a result of speech analysis, which contains one or more recognized voice command(s), is provided. A method for processing natural language can be used for this purpose. In particular, a computer linguistics algorithm can be applied to the audio signal or the speech input for this purpose. One possibility of processing the speech input formulated in natural language for the provision of the result of speech analysis is converting the speech input formulated in natural language into text (structured speech, therefore), by way of a text-to-speech (software) module. A further analysis for the provision of the result of speech analysis, for example by way of latent semantic indexing (LSI for short), can then ascribe meaning to the text. Speech analysis and, in particular, an understanding of the natural language contained in the speech input (natural language understanding, NLU) can then occur.

Providing the (adjusted) visualization image can comprise an output of the (adjusted) visualization image to the user via a user interface, a transfer of the (adjusted) visualization image to a storage facility (for instance a PACS system) and/or embedding of the adjusted visualization image in a medical report.

According to one implementation, the method comprises receiving one or more gesture command(s) of a user, with the context data being provided based upon the gesture commands of the user.

Gesture commands can comprise, for example, the user pointing to or looking at a visualization area of the visualization image. Gesture commands can be detected, for example, by way of a suitable camera apparatus and be registered with the visualization image. Gesture and look detection algorithms that are known per se can be used in this case.

According to one implementation of at least one embodiment, the method comprises receiving one or more combined gesture command(s) and speech input(s) of a user, with the context data being provided based upon the gesture commands of the user.

Consequently, the user can influence the visualization by way of combined gestures and voice control. For example, he can point to a visualization area of the visualization image and also give an instruction (for example "make this area brighter").

According to one embodiment, the context data has information about one or more preference(s) of the user in respect of the visualization of the volume data.

A visualization can be proactively adjusted to the preferences of the user by taking account of the user preferences. The user has to make even fewer adjustments, and this makes the method easier to operate and, in particular in clinical practice, more useful.

According to one embodiment, the context data comprises one or more electronic document(s) containing natural language and/or text relating to the object to be visualized. The documents can comprise, in particular, one or more medical report(s) and/or medical guideline(s).

A presumably expedient visualization can be determined by the evaluation of clinical reports and/or medical guidelines and can be automatically offered to the user.

According to some implementations of embodiments, the electronic documents can also comprise, for example, doctor's letters, metadata of the volume data (for example DICOM attributes), one or more clinical ontologies such as RadLex or SNOMED, and/or comparative medical studies.

According to some implementations of embodiments, the method also comprises:

providing an evaluation algorithm for application to the volume data, with the evaluation algorithm being designed to provide an analytical result on application to volume data;

generating an analytical result by applying the evaluation algorithm to the volume data;

providing the context data also based upon the analytical result.

An analytical result can be directly taken into account in the visualization due to this step. If the evaluation algorithm is designed, for example, to detect lesions in the lungs, the mapping indication and/or the mapping rule can be determined in such a way that the lesions are emphasized accordingly. An evaluation algorithm can generally be designed to evaluate volume data or the image information contained therein for a specific, in particular medical problem. An evaluation algorithm can thus be designed, for example, to recognize and classify objects, to measure geometries, and/or to mark objects.

According to one implementation of at least one embodiment, providing the evaluation algorithm also comprises:

providing a plurality of different evaluation algorithms, which is in each case designed to provide a specific analytical result on application to volume data;

selecting the evaluation algorithm from the different evaluation algorithms based on the volume data and/or the context data.

Consequently, a suitable evaluation algorithm can be automatically selected based upon the clinical context or even a verbal user input, and this further improves the convenience.

According to one embodiment, one or more of the electronic document(s) can be retrieved from a database. In the medical application, for example an electronic patient identifier, such as an ID or a name of the patient, can be extracted from the volume data for this purpose, with which identifier the database can then be searched for relevant documents. The electronic documents can be part of an electronic file of the patient. The database can be designed, for example, to store electronic patient files of a plurality of patients. The database can be, for example, part of a hospital information system.

According to one embodiment, the volume data is not provided in advance but retrieved from a suitable database based upon the context data. Based upon the context data, a suitable series, suitable volume data can be retrieved thereby, with which, for example, the mapping indication may be implemented especially well.

According to one embodiment, the visualization image has a series of a plurality of individual images, which visualize the volume data or a series of volume data in a time-resolved manner. In other words, the visualization image can contain a video.

According to one embodiment, the mapping indication and/or the mapping rule is determined with a configuration algorithm. The configuration algorithm can comprise, in particular, a computer linguistics algorithm.

The configuration algorithm can be understood, in particular, as a computer program product, which is designed for determination of the mapping indication or the mapping rule. The configuration algorithm can have program components in the form of one or more instruction(s) for a processor for determination of the mapping indication or the mapping rule. The configuration algorithm can be provided, for example, in that it is held available in a storage facility or is loaded into a main memory of a suitable data processing facility or is generally provided for application or use.

The computer linguistics algorithm can be designed, in particular, for algorithmic processing of natural language in the form of text or voice data with the aid of a computer. The computer linguistics algorithm can be designed, in particular, to recognize or to identify in the context data words relevant to the visualization and their context, and thus transfer them into a mapping indication or to generate a mapping indication.

According to one embodiment, the configuration algorithm, and in particular the computer linguistics algorithm, has one (or more) trained function(s).

A trained function generally maps input data onto output data. Here the output data can still depend, in particular, on one or more parameter(s) of the trained function. The one or more parameter(s) of the trained function can be determined and/or adjusted by training. Determining and/or adjusting of the one parameter or the plurality of parameters of the trained function can be based, in particular, on a pair of training input data and associated training output data, with the trained function being applied to training input data for the generation of training mapping data. In particular, determining and/or adjusting can be based on a comparison of the training mapping data and the training output data. In general, a trainable function, in other words a function with parameters that have not yet been adjusted, is also referred to as a trained function.

Other terms for trained function are trained mapping rule, mapping rule with trained parameters, function with trained parameters, algorithm based on artificial intelligence, machine learning algorithm. One example of a trained function is an artificial neural network. Instead of the term "neural network" the term "neural net" can also be used. Basically, a neural network is constructed like a biological neural network such as a human brain. In particular, an artificial neural network comprises an input layer and an output layer. It can also comprise a plurality of layers between input and output layers. Each layer comprises at least one, preferably a plurality of nodes. Each node can be taken to mean a biological processing unit, for example a neuron. In other words, each neuron corresponds to an operation, which is applied to input data. Nodes of a layer can be connected by edges or connections to nodes of other layers, in particular by directed edges or connections. These edges or connections define the flow of data between the nodes of the network. The edges or connections are associated with a parameter, which is often referred to as a "weight" or "edge weight". These parameters can regulate the importance of the output of a first node for the input of a second node, with the first node and the second node being connected by an edge.

In particular, a neural network can be trained. In particular, training of a neural network is carried out based upon the training input data and associated training output data according to a "supervised" learning technique, with the known training input data being input into the neural network and the output data generated by the network being compared with the associated training output data. The artificial neural network learns and adjusts the edge weights for the individual nodes independently as long as the output data of the last network layer does not sufficiently correspond to the training output data.

In particular, a trained function can also be deep neural network or deep artificial neural network.

According to some implementations of at least one embodiment, determining the mapping rule comprises providing a trained function, which is adjusted in such a way that, based on volume data and context data, it provides a mapping rule suitable for the context data, and providing the mapping rule by applying the trained function to the context data and the volume data.

According to some implementations of at least one embodiment, the trained function has a neural network and in particular a convolutional neural network.

In particular, the convolutional neural network can be designed as a deep convolutional neural network. The neural network has one or convolutional layer(s) and one or more deconvolutional layer(s). In particular, the neural network can comprise a pooling layer. A neural network can be especially efficiently used for the derivation of a mapping rule through the use of convolutional layers and/or deconvolutional layers since only a few edge weights (namely the edge weights corresponding to the values of the convolutional core) have to be determined despite many connections between node layers. With an identical number of training data items, the accuracy of the neural network can also be improved thereby.

According to one example embodiment, the trained function has a U-net architecture.

A U-net architecture is based on convolutional neural networks, with pooling layers being replaced by "upsampling" layers. In addition, jump links are provided, which enable context information to be input, for example from convolutional layers, directly into deconvolutional layers. Faster processing can thus be achieved through the use of a U-net architecture and less training data is required.

According to a further embodiment, a computer-implemented method for providing a trained function for determining a mapping rule is disclosed. The method comprises:

providing training input data, wherein the training input data has context data containing natural language and/or text in respect of the visualization of a three-dimensional object and volume data representing the three-dimensional object;

providing training output data, wherein the training output data has a mapping rule for the generation of a suitable two-dimensional visualization image by mapping the volume data;

generating a training mapping rule by applying the trained function to the training input data;

comparing the training mapping rule with the training output data;

adjusting the trained function based upon the comparison.

Training input and training output data can be provided, for example, in that suitable mapping rules for particular volume data and context data are determined by a visualization expert. Consequently, the trained function is rendered capable of reproducing suitable mapping rules for unknown volume data/context data and thus saves a user who is less experienced in respect of visualization the time-consuming task of finding suitable visualization parameters.

The use of a trained function should be understood as being merely optional. Alternatively, other solutions can also be pursued, such as a solution based on strictly predefined rules.

According to a further embodiment, an apparatus is disclosed for the provision of a two-dimensional visualization image having a plurality of visualization pixels for visualization of a three-dimensional object represented by volume data for a user, which apparatus comprises:

an interface, which is designed to receive the volume data and context data containing natural language in respect of the visualization of the three-dimensional object;

a configuration module, which is designed to:
determine a mapping indication based on the context data (and optionally on the volume data), wherein the mapping indication comprises information about a mapping of the volume data, which is suitable based on the context data, onto the visualization image; and
determine a mapping rule based on the mapping indication; and a visualization module, which is designed to:
map the volume data onto the visualization pixels using the mapping rule for the creation of the visualization image; and
provide the visualization image.

The configuration module and/or the visualization module of an embodiment can be part of an computing facility. The configuration module can be designed to carry out the configuration algorithm. The visualization module can be designed to carry out the image synthesis algorithm.

The computing facility can be designed as a central or decentral computing facility. The computing facility can have one or more processor(s). The processors can be designed as a central processing unit (CPU for short) and/or as graphics processing unit (GPU for short). The computing facility can be designed as what is known as a system-on-a-chip (SoP for short), which controls all functions of a device. Alternatively, the computing facility can be implemented as a local or Cloud-based processing server.

The interface of an embodiment can be designed generally for the exchange of data between the computing facility and further components. The interface can be implemented in the form of one or more individual data interface(s), which can have a hardware and/or software interface, for example a PCI bus, a USB interface, a Firewire interface, a ZigBee interface or a Bluetooth interface. The interface can also have an interface of a communications network, wherein the communications network can have a Local Area Network (LAN), for example an Intranet or a Wide Area Network (WAN). The one or more data interface(s) can accordingly have a LAN interface or a Wireless LAN interface (WLAN or Wi-Fi).

The advantages of the proposed apparatus substantially match the advantages of the proposed method. Features, advantages or alternative embodiments can likewise be transferred to the other claimed subject matters, and vice versa.

According to one embodiment, the apparatus also has a storage facility, which is designed to store context data and provide it via the interface.

The storage facility can be, in particular, part of what is known as a Picture Archiving and Communication system (PACS). In addition or alternatively, the storage facility can be part of a medical information system, such as a hospital or laboratory information system.

The invention relates in a further embodiment to a computer program product, which comprises a program and can be loaded directly into a storage device of a programmable computing facility and has program code/segments, for example libraries and auxiliary functions, in order to carry out an embodiment of a method for the visualization of a three-dimensional object in particular according to the embodiment when the computer program product is run.

Furthermore, the invention relates in a further embodiment to a computer program product, which comprises a program and direct can be loaded directly into a storage device of a programmable computing facility and has program code/segments, for example libraries and auxiliary functions, in order to carry out a method for the provision of a trained function in particular according to the embodiment when the computer program product is run.

The computer program products of an embodiment can comprise software with a source code, which still has to be compiled and linked or which only has to be interpreted, or an executable software code, which for execution only has to be loaded into the processing unit. As a result of the computer program products the method can be carried out quickly, repeatedly in an identical manner and robustly. The computer program products are configured such that they can carry out the inventive method steps by way of the computing facility. The computing facility has to have in each case the requirements such as an appropriate main memory, an appropriate processor, an appropriate graphics card or an appropriate logic unit, so the respective method steps of an embodiment can be efficiently carried out.

The computer program products are stored, for example in an embodiment, on a computer-readable storage medium or saved on a network or server from where they can be loaded into the processor of the respective computing facility, which is directly connected to the computing facility or can be designed as part of the computing facility. Furthermore, control information of the computer program products can be stored on a computer-readable storage medium. The control information of the computer-readable storage medium can be configured in such a way that it carries out an inventive method when the data carrier is used in an computing facility. Examples of computer-readable storage medium are a DVD, a magnetic tape or a USB stick on which electronically readable control information, in particular software, is stored. When this control information is read from the data carrier and stored in an computing facility, all inventive embodiments of the previously described method can be carried out. The invention can thus also start from the computer-readable medium and/or the computer-readable storage medium. The advantages of the proposed computer program product or the associated computer-readable media substantially match the advantages of an embodiment of the proposed method.

FIG. 1 shows a system 1 for the provision of a visualization image for a user N according to one embodiment of the invention in a schematic representation.

The system 1 has a storage unit 60 and a database 70, a visualization module 23 and a configuration module 22, which have a data connection to each other.

The storage unit 30 is designed to store volume data. The volume data is, in particular, image data, which was acquired from patients using medical imaging modalities. The volume data is linked to one patient in each case thereby.

The database 70 is designed to store context data KD for a visualization of the volume data. The context data KD can comprise, in particular, patient context data. This patient context data is linked to one patient in each case and can consequently be assigned to the volume data. The patient context data can comprise, for example, medical findings, reports, doctor's letters and the like. The patient context data can be provided, for example, in the form of an electronic medical record. Furthermore, the context data KD can include user context data, which is specific to a user N of the system 1. For example, the user context data can contain user preferences in respect of the visualization of volume data. In addition, the context data can contain higher-order clinical data, which can comprise, for example, one or more medical guideline(s).

The storage unit 60 and/or the database 70 can be designed as distributed storage facilities and comprise a plurality of individual storage devices.

An additional source (apart from the database 70) for context data KD can be speech inputs of the user N. Generally, the context data KD has elements, which include natural language and/or text (for example in the form of the speech inputs or as text for example in the patient context data and/or clinical guidelines).

The configuration module 22 is designed to determine a suitable visualization of volume data VD for a patient based on an analysis of the context data KD and to derive a mapping rule for the visualization module 23 therefrom. For this purpose, the configuration module 22 is designed, in particular, to evaluate the elements natural language and/or text in the context data KD. The configuration module 22 can implement an appropriately configured algorithm for this purpose. This algorithm can comprise a computer linguistics algorithm for processing natural language and/or text.

The visualization module 23 is designed to map volume data VD onto the visualization image based upon a mapping rule and to thus generate a visualization. The visualization module 23 can implement a visualization algorithm for this purpose.

If a user N wishes to see a medical record in order, for example, to make a medical diagnosis, the user N can be inventively assisted in this as follows. Firstly, volume data VD is provided in step S10.

In a step S20, the configuration module 22 automatically, or in response to a user activation, loads or collects relevant context data KD. The configuration module 22 can, for example, receive a speech input from the user N or query the database 70 for relevant context data for this purpose.

Based upon the context data, the configuration module 10 is designed to determine a mapping indication, which shows which type of mapping of the volume data is probably expedient or desired in the present case for the user N (step S30). The mapping indication can show which perspective, which organ, which volume data or generally which mapping parameters will probably be required. In one example, it can emerge from the context data, for example, that a time-resolved video sequence of the heartbeat should be rendered. This can be the case, for example, when the context data points to a pending cardiological examination of the patient.

In an alternative embodiment, the volume data is already predefined (for instance by a user selection) and taken into account on determination of the mapping indication.

Based upon the mapping indication, the configuration module 10 then generates a mapping rule for the visualization module 20 in step S40 and inputs it therein. Based upon this mapping rule, the visualization module 20 then generates a visualization in step S50 and provides the user N with it in step S60.

In a step S70, the user N then has the option of providing the configuration module 10 with feedback via the visualization image, which feedback the configuration module 22 can then use for adjustment of the mapping indication and the mapping rule AV. Consequently, the user N is given the option of easily influencing the visualization module 23 by speech input without having to intervene in the parameter control thereof themselves.

Figure 2:
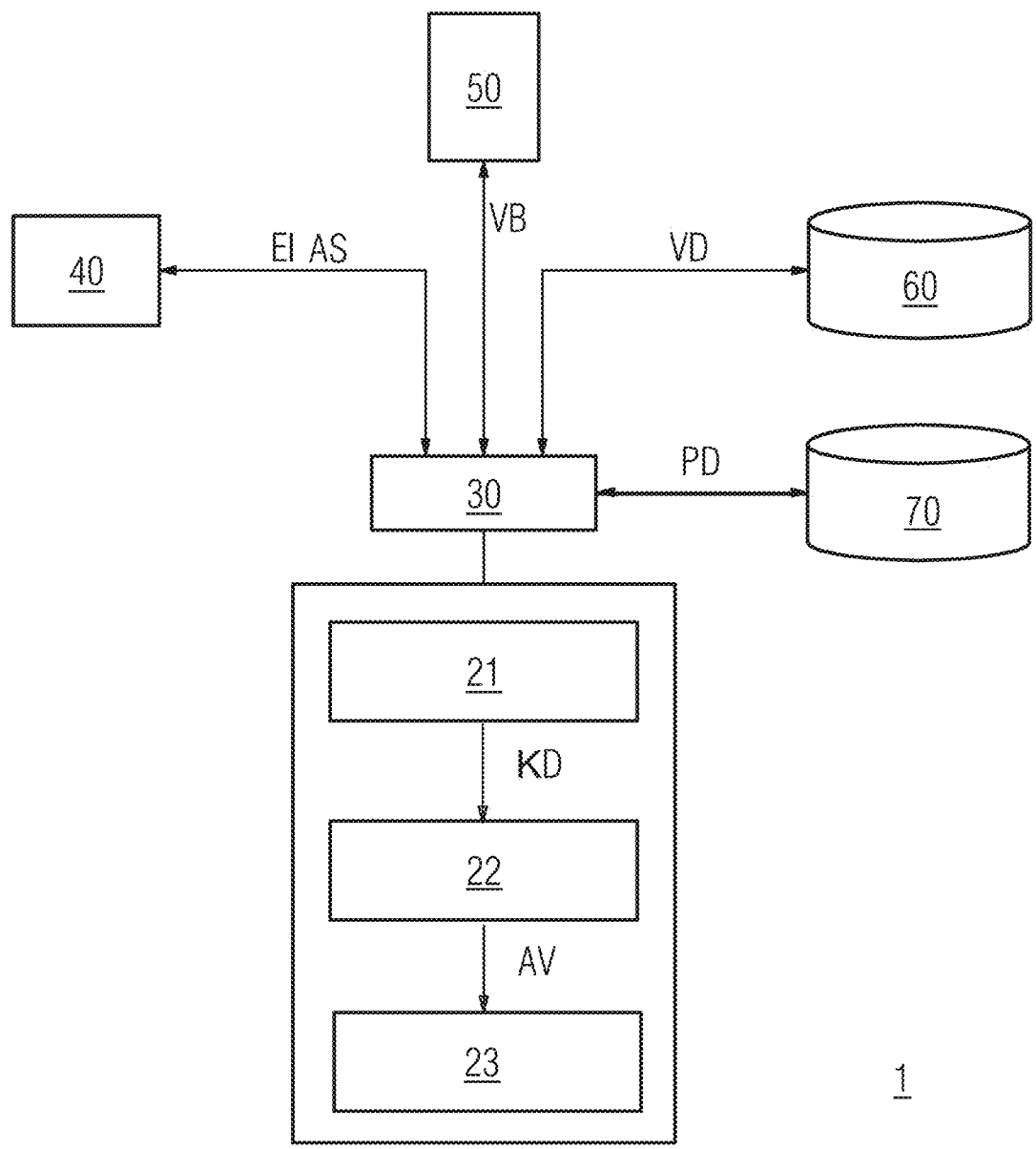
FIG. 2 shows a schematic representation of a further embodiment of a system for the visualization of a three-dimensional object.

FIG. 2 represents a system 1 for the visualization of a three-dimensional object according to a further embodiment. The system 1 has an computing facility 20, an interface 30, a detection apparatus 40, a rendering apparatus 50, a storage unit 60 and a database 70. The computing facility 20 is basically designed for calculation of a visualization image VB of a three-dimensional object based upon volume data VD describing the three-dimensional object. The computing facility 20 can be provided with the volume data VD from the storage unit 60 via the interface 30.

The storage unit 60 can be designed as a central or decentral database. The storage unit 60 can be, in particular, part of a server system. The storage unit 60 can be, in particular, part of what is known as a Picture Archiving and Communication system (PACS). The volume data VD can have been generated by a medical imaging method. For example, the volume data VD can have been generated by radioscopy, computed tomography (CT), magnetic resonance tomography (MR), ultrasound and/or positron emission tomography (PET). The volume data VD can be formatted, for example, in the DICOM format. DICOM stands for Digital Imaging and Communications in Medicine and denotes an open standard for the storage and exchange of information in medical image data management. The volume data VD has a three-dimensional data set comprising a plurality of volume pixels, what are known as voxels. The voxel values can be obtained, for example, by the medical imaging method and conventionally constitute a measure of the local density of the three-dimensional object at the location of the voxels. Providing the volume data VD can comprise, for example, loading the volume data VD into a main memory (not shown) of the computing facility 20.

The database 70 can be, in particular, part of a medical information system, such as a hospital information system, a PACS system, a laboratory information system and/or further medical information systems. The database 70 can also be designed as what is known as a Cloud storage device. The database 70 can be designed to store patient data PD. Patient data PD can be, for example, examination results, which are not based on medical imaging. In addition, patient data PD can comprise text data sets, such as structured and unstructured medical reports. Alternatively or in addition, the patient data PD can also comprise an electronic medical record (or EMR for short) of the patient. In alternative embodiments, the database 70 can also be integrated in the storage facility 50. Furthermore, patient data PD can be incorporated in the volume data VD for example as metadata.

The computing facility 20 is designed to take into account context data KD in the calculation of a visualization or mapping of the three-dimensional object. For this purpose, the computing facility 20 can be provided with an audio signal AS via the interface 30, which audio signal AD can comprise a speech input of the user N. Furthermore, the computing facility 20 can be provided with acquisition information EI via the interface 30, which acquisition information EI contains information about where the user N is currently looking or whether the user N is currently gesturing. The audio signal AS and the acquisition information EI are provided by the detection apparatus 40. The detection apparatus 40 can accordingly be configured to detect a viewing direction of a user N. For this purpose, it can have optical detection device(s) such as cameras, which detect the eye area and/or the pupil position and/or the K head position of the user N. The acquisition information EI can then include, for example, image data of an eye area, a pupil position and/or a head position. The detection apparatus 40 can also be configured to detect a gesture of a user N. For this purpose, it can have optical detection device(s) such as cameras, which detect a gesture, for instance with a hand, of the user N. Furthermore, the detection apparatus 40 can have an acoustic input apparatus. The acoustic input apparatus serves to record or acquire an audio signal AS, to record spoken sounds, therefore, which are generated by the user N of the system 1. The acoustic input apparatus can be implemented, for example, as a microphone. The acoustic input apparatus can be stationarily arranged, for example, in an operating space. Alternatively, the acoustic input apparatus can also be implemented to be portable, for example as a microphone of a headset, which can be carried along by the N. Furthermore, the computing facility 20 can request patient data PD from the database 70 and this can be searched for context data KD. Text-mining algorithms for example can be used for this purpose.

Once the visualization image VB has been calculated it should be displayed to the user N. For this purpose, the rendering apparatus 50 is provided with the visualization image VB via the interface 30. The rendering apparatus 50 can have one or more screen and/or projection facility/ies, which are designed for the rendering of the visualization image VB for the user N. In particular, the rendering apparatus 50 can be implemented as an image representation system of augmented reality glasses. Alternatively, the rendering apparatus 50 can have a screen of a PC, laptop, tablet or smartphone.

The interface 30 can have one or more individual data interface(s), which guarantee the exchange of data between the components 20, 40, 50, 60, 70 of the system 1. The one or more data interface(s) can have a hardware and/or software interface, for example a PCI bus, a USB interface, a Firewire interface, a ZigBee interface or a Bluetooth interface. The one or more data interface(s) can have an interface of a communications network, wherein the communications network can have a Local Area Network (LAN), for example an Intranet or a Wide Area Network (WAN). The one or more data interface(s) can accordingly have a LAN interface or a Wireless LAN interface (WLAN or Wi-Fi).

The computing facility 20 can comprise, for example, a processor, for example in the form of a CPU or the like. The computing facility 20 can be designed as a central control unit, for example as a control unit with one or more processor(s). According to further implementations, functionalities and components of the computing facility 20 can be distributed in a decentralized manner over several arithmetic units or controllers of the system 1.

For calculation of the visualization image VB based on the input data the computing facility 20 can have different elements 21, 22, and 23. The element 21 can be understood as a context data provision module. Element 21 can implement or control an algorithm which is designed to determine a viewing direction of the user N or recognize a gesture control of the user N based on the acquisition information EI. For this purpose, the acquisition information EI is evaluated by element 21 and related to the visualization image VB displayed or to be displayed. For this purpose, it is possible to draw on, for example, a suitable registration— for instance between the detection apparatus 40 and the rendering apparatus 50. Element 21 can also implement or control an algorithm, which extracts one or more voice command(s) of the user N from an audio signal AS and provides it/them as context data KD. Element 21 can also implement or control an algorithm, which retrieves relevant patient data PD from the database 70 and searches for information relevant to the visualization and provides it as context data KD.

The element 22 can be understood as a configuration module, which suitably configures the visualization based on the volume data VD and the context data KD. In particular, the element 22 can cause an algorithm to be applied, which determines a mapping indication based on the context data KD and the volume data, under which indication the visualization will be considered. In other words, the mapping indication comprises a context, in particular a medical one, which is relevant to the visualization. Furthermore, the algorithm can be designed to determine a mapping rule AV based on the mapping indication, which in turn is suitable for generating a mapping of the volume data VD suitable for the mapping indication.

The element 23 can be understood as a volume rendering engine. The element 23 can implement or control an image synthesis algorithm, which is designed to map the volume data VD onto the visualization image VB or the pixels of the visualization image VB. The pixels of the visualization image VB will be called visualization pixels below. For calculation of the mapping onto the visualization pixels the image synthesis algorithm can have different visualization modules, which can be selectively activated and deactivated, and in particular for each visualization pixel, and/or can be adjusted in terms of their computing effort. The visualization modules can refer, for example, to different approaches for calculation of a visualization image VB. For example, the image synthesis algorithm can comprise a ray casting module in which visualization pixels VP are calculated with the method of ray casting. Furthermore, the image synthesis algorithm can have a path tracing module in which visualization pixels are calculated according to the method of path tracing. In addition, the visualization modules can refer to supplementary mapping effects. These supplementary mapping effects can comprise, in particular with ray casting methods, for example ambient occlusion effects, shadow effects, translucence effects, color bleeding effects, surface shading, complex camera effects and/or lighting effects due to random ambient lighting conditions. Overall, the element 23 is thereby designed in such a way that the computing effort, and therewith the quality of the mapping, can be selectively set for each individual visualization pixel VP.

The performed division of the computing facility 20 into elements 21-23 serves solely to simplify the explanation of the mode of operation of the computing facility 20 and should not be understood as limiting. The elements 21-23 or their functions can also be combined into one element. The elements 21-23 can be understood in particular also as computer program products or computer program segments, which when run in the computing facility 20 implement one or more of the method step(s) described below.

Figure 3:
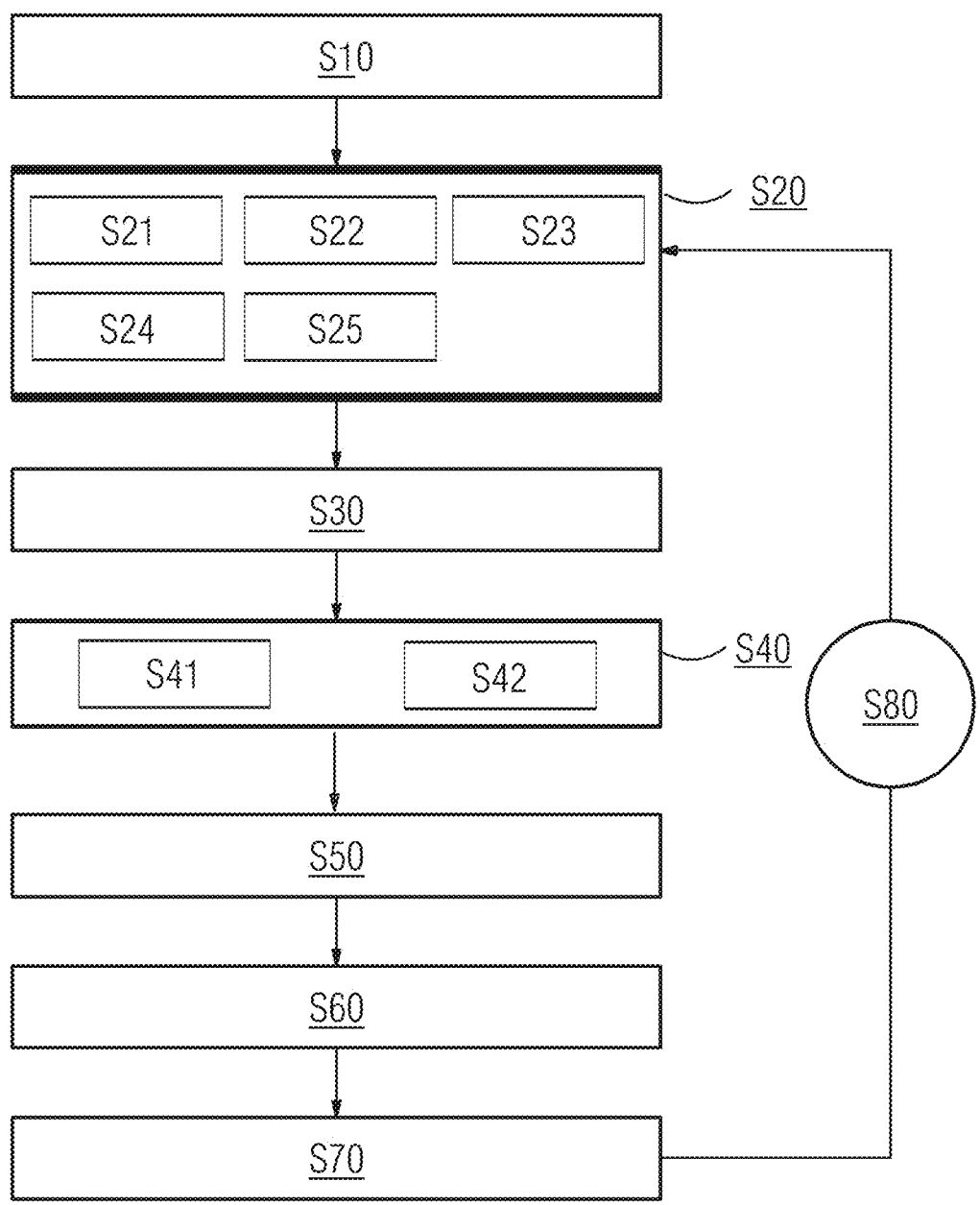
FIG. 3 shows a flowchart of a method for the visualization of a three-dimensional object according to one embodiment.

FIG. 3 represents a schematic flowchart of a method for visualization of a three-dimensional object. The order of the method steps is limited by neither the represented sequence nor by the chosen numbering. The order of the steps can thus optionally be interchanged and individual steps can be omitted.

A first step S10 is directed toward providing the volume data VD. The provision can be implemented by a retrieval of the volume data VD from the storage unit 60 and/or loading of the volume data VD into the computing facility 20.

In a next step S20, context data KD is provided for the visualization. The context data KD can comprise:
 one or more voice command(s) of the user N,
 one or more item(s) of information from patient data PD,
 one or more user preference(s) for the visualization,
 one or more gesture(s) of the user N, and/or
 an analytical result of an image data evaluation algorithm applied to the volume data VD.

Accordingly, step S20 can have a plurality of optional sub-steps. A sub-step S21 can be directed to detecting one or more voice command(s) in the audio signal AS and the provision of the voice commands as context data KD. A sub-step S22 can be directed to detecting one or more gesture control command(s) in the acquisition information EI and the provision of the gesture control commands as context data KD. A sub-step S23 can be directed to retrieving patient data PD from the database 70 (or the storage unit 60), an analysis of the patient data for the provision of a text analysis result and the provision of the text analysis result as context data KD. A sub-step S24 can be directed to retrieving user preferences from the database 70 (or the storage unit 60) and the provision of the user preferences as context data KD. A sub-step S25 can be directed to applying a selection of an evaluation algorithm, applying the evaluation algorithm for the generation of an analysis result and providing the analysis result as context data KD.

Speech analysis algorithms, text analysis algorithms, image analysis evaluation algorithms and the like, which are known per se, can be used for the provision of the context information KD.

In a next step S30, a mapping indication is determined based upon the context data KD. The mapping indication indicates which visualization is suitable or expedient for the user N in view of the volume data VD and the context data. For this purpose, a trained function can be applied to the volume data VD and the context data KD in step S30, which function was designed to derive a corresponding mapping indication based on the volume data VD and the context data KD.

In step S40, a mapping rule AV is then determined based upon the mapping indication, which rule is capable of mapping the volume data VD in accordance with the mapping indication onto the visualization image. Different parameters for mapping the volume data VD can be suitably adjusted for this purpose, such as: a perspective, a scene illumination, a transfer function, a transparency of one or more region(s) of the volume data, a cutting plane through the volume data, a region of interest within the volume data, and/or one or more additional item(s) of information for overlaying in the visualization image.

Optionally, one or more specific object(s) can be selected in step S40 for visualization (step S41). In particular, first of all objects can be identified in the volume data VD and then the context data KD selected accordingly for the visualization (or not selected and thus not represented). Furthermore, virtual objects can also be supplemented from other volume data or further sources and also be mapped in the visualization.

Optionally, specific volume data sets can also be selected in step S40 from the available volume data VD of a patient (step S42). Thus, depending on context data KD and mapping indication, for example volume data sets can be selected, which represent a relevant problem from the context data KD/the mapping indication especially well. If the context data KD indicates, for example, that a vessel structure should be represented in the visualization image, angiography data sets can be sought in the volume data VD and can (optionally additionally) form the basis of the visualization. A plurality of different volume data sets can also be explicitly combined in order to obtain a suitable visualization (for instance dual energy data sets in CT imaging).

The trained function can in turn also be suitably designed for determination of the mapping rule based on the mapping indication. Alternatively, the trained function or the processing generally can also be designed in such a way that the mapping rule is determined directly based upon the context data KD. Step S30 can then also be omitted accordingly and/or be included in step S40.

In step S50, the visualization image VB is then created with the mapping rule AV. In step S60, the rendering apparatus 50 is provided with the finished visualization image VB via the interface 30. In step S70, the rendering apparatus 50 displays the visualization image VB to the user. Steps S60 and S70 are optional and can be omitted.

Step S80 represents an optional repetition step. Once the visualization image VB has been displayed to the user N, the processing jumps via step S80 again to step S20 and the context data KD is acquired once again. This primarily takes account of the case where the user N, based upon the visualization image VB, has verbalized a voice command for adjusting same. On this basis, a new mapping rule AV is calculated in step S40 and the visualization image VB is updated in the steps S50 and optionally S60, and S70. The calculation of the visualization image VB can be continuously adjusted to the instantaneous context by the repetition step S80.

Figure 4:
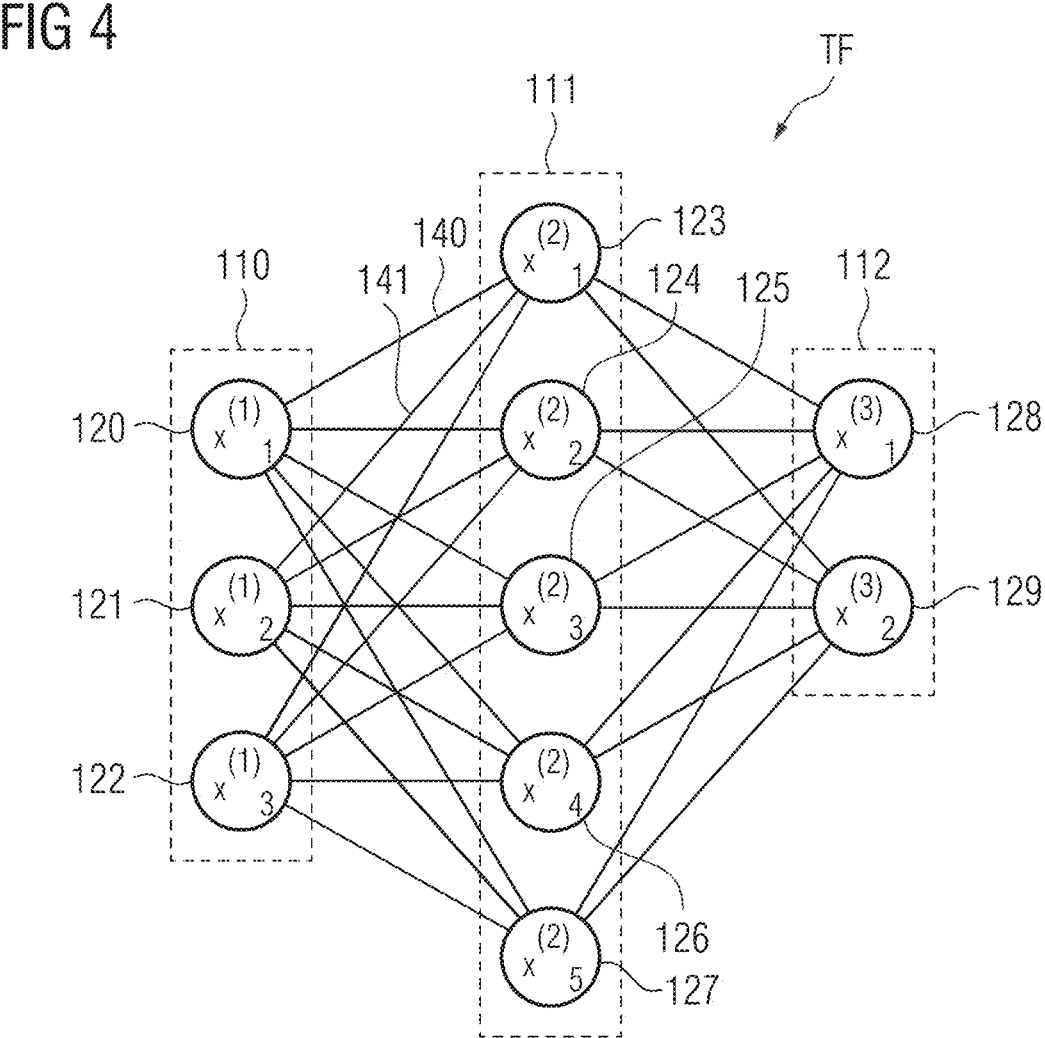
FIG. 4 shows a trained function for generating an improved visualization image.

FIG. 4 shows an example representation of a trained function TF, as can be used in step S30 or S40 for determination of a mapping rule AV. The trained function TF receives the context data KD as an input and outputs the mapping rule AV as an output, in other words control commands for actuation of the visualization module 23, therefore.

In the illustrated example embodiment, the trained function TF is designed as a neural network. The neural network can also be referred as an artificial neural network or a neuronal network.

The neural network 100 comprises nodes 120, . . . , 129 and edges 140,141, with each edge 140,141 being a directed connection of a first node 120, . . . , 129 to a second node 120, . . . , 129. In general, the first node 120, . . . , 129 and the second node 120, . . . , 129 are different nodes; it is also possible that the first node 120, . . . , 129 and the second node 120, . . . , 129 are identical. An edge 140,141 of a first node 120, . . . , 129 to a second node 120, . . . , 129 can also be referred to as an incoming edge for the second node and as an outgoing edge for the first node 120, . . . , 129.

The neural network 100 responds to input values $x^{(1)}_1$, $x^{(1)}_2$, $x^{(1)}_3$ relating to a large number of input nodes 120, 121, 122 of the input layer 110. The input values $x^{(1)}_1$, $x^{(1)}_2$, $x^{(1)}_3$ are applied in order to generate one or a large number of output(s) $x^{(3)}_1$, $x^{(3)}_2$. The node 120 is connected for example via an edge 140 to the node 123. The node 121 is connected for example via the edge 141 to the node 123.

In this example embodiment, the neural network 100 learns by adjusting the weighting factors $w_{i,j}$ (weights) of the individual nodes based on training data. Possible input values $x^{(1)}_1$, $x^{(1)}_2$, $x^{(1)}_3$ of the input nodes 120,121,122 can be, for example, the individual field variables $\tilde{E}_{BC}$, $\tilde{H}_{BC}$, $\tilde{E}_i$, $\tilde{H}_i$ and/or examination information UI (if present).

The neural network 100 weights the input values of the input layer 110 based on the learning process. The output values of the output layer 112 of the neural network 100 preferably correspond to field information FI, based upon which the electrical and/or magnetic field underlying the signature S may be at least partially suppressed. The output can be made via an individual or a large number of output node(s) $x^{(3)}_1$, $x^{(3)}_2$ in the output layer 112.

The artificial neural network 100 preferably comprises a hidden layer 111, which comprises a large number of nodes $x^{(2)}_1$, $x^{(2)}_2$, $x^{(2)}_3$. A plurality of hidden layers can be provided, with one hidden layer using output values of a different hidden layer as input values. The nodes of a hidden layer 111 perform mathematical operations. An output value of a node $x^{(2)}_1$, $x^{(2)}_2$, $x^{(2)}_3$ corresponds to a non-linear function f of its input values $x^{(1)}_1$, $x^{(1)}_2$, $x^{(1)}_3$ and the weighting factors $w_{i,j}$. After receiving input values $x^{(1)}_1$, $x^{(1)}_2$, $x^{(1)}_3$, a node $x^{(2)}_1$, $x^{(2)}_2$, $x^{(2)}_3$ carries out a summation of a multiplication of each input value $x^{(1)}_1$, $x^{(1)}_2$, $x^{(1)}_3$ weighted with the weighting factors wi,j, as determined by the following function:

$$x_j^{(n+1)} = f(\Sigma_i x_i^{(n)} \cdot w_{i,j}^{(m,n)}).$$

The weighting factor $w_{i,j}$ can be in particular a real number, in particular lie in the interval from [−1;1] or [0;1]. The weighting factor $w_{i,j}^{(m,n)}$ designates the weight of the edge between the $i^{th}$ nodes of an $m^{th}$ layer 110,11,112 and a $j^{th}$ node of the $n^{th}$ layer 110,111,112.

In particular, an output value of a node $x^{(2)}_1$, $x^{(2)}_2$, $x^{(2)}_3$ is formed as a function f of a node activation, for example a sigmoidal function or a linear ramp function. The output values $x^{(2)}_1$, $x^{(2)}_2$, $x^{(2)}_3$ are transferred to the output node(s) 128,129. A summation of a weighted multiplication of each output value $x^{(2)}_1$, $x^{(2)}_2$, $x^{(2)}_3$ is calculated again as a function of the node activation f, and therewith the output values $x^{(3)}_1$, $x^{(3)}_2$.

The neural network TF shown here is a feedforward neural network in which all nodes 111 process the output values of a previous layer in the form of its weighted sum as input values. Of course, inventively, other types of neural network can also be used, for example feedback networks, in which an input value of a node can simultaneously also be its output value.

The neural network TF can be trained by way of a method of supervised learning in order to provide the field information FI. A known procedure is back propagation, which can be applied to all example embodiments of the invention. During training, the neural network TF is applied to training input data or values and has to generate corresponding, known training output data or values. Mean square errors (MSE) are iteratively calculated between calculated and expected output values and individual weighting factors are adjusted until the deviation between calculated and expected output values lies below a predetermined threshold.

For the provision of training data, for example visualization parameters or mapping rules AV can be drawn on, which were created by visualization experts for a particular medical context and for particular volume data. In addition, mapping rules AV can be drawn on, which a user N deemed good in the past or which he has at least not rectified further.

In some implementations a user input can also be received, which refers to the visualization image VB. The user input can comprise, for example, a command to change one or more visualization parameter(s). Furthermore, the user input can comprise an acceptance of the visualization image for the further workflow. The trained function TF can then be adjusted further based upon such a user input by commands for adjustment being penalized on further training of the trained function and the acceptance of a visualization image VB resulting, with further training, in a reinforcement.

Figure 5:
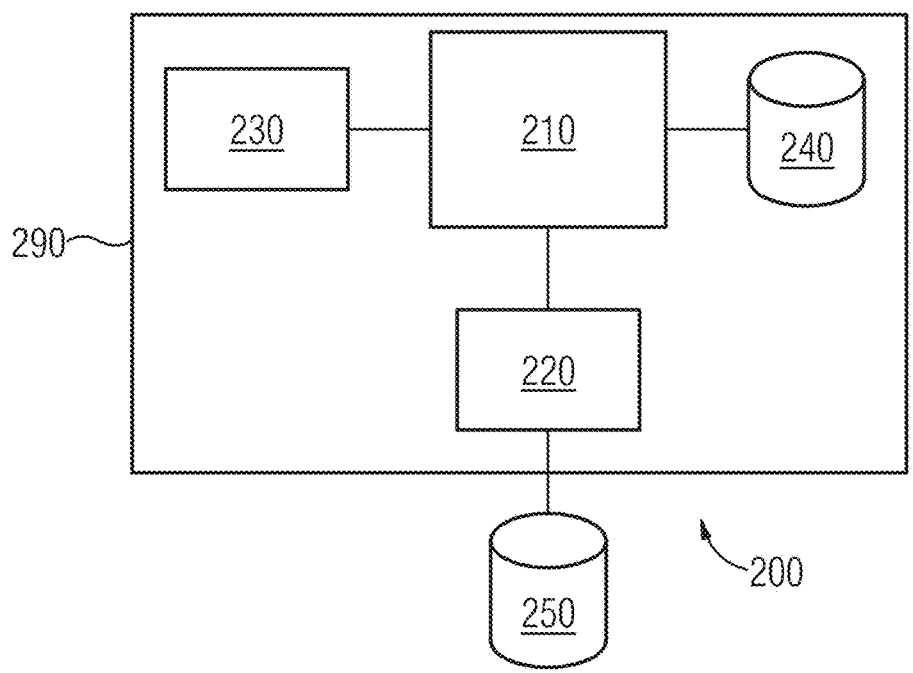
FIG. 5 shows a schematic representation of an embodiment of a system for providing the trained function.

FIG. 5 shows an embodiment of a system 200 for training or providing the trained function TF. The system comprises a processor 210, an interface 220, a main memory 230, a storage facility 240 and a database 250. The processor 210, the interface 220, the main memory 230 and the storage facility 240 can be designed as a computer 290. The processor 210 controls the operation of the computer 290 on training of the trained function TF. In particular, the processor 210 can be designed in such a way that it carries out the method steps represented in FIG. 9. The instructions can be stored in the main memory 230 or in the storage facility 240 and/or be loaded into the main memory 230 when execution of the instructions is desired. The storage facility 240 can be designed as a local storage device or a remote storage device, which can be accessed over a network. The method steps represented in FIG. 9 can be defined by computer program products, which are stored in the main memory 230 and/or the storage facility 240.

The database 250 can be implemented as a Cloud storage device or local storage device, which is connected to the computer 290 via the wireless or wired interface 220. The database 250 can, in particular, also be part of the computer 290. The database 250 serves as an archive for the (training) volume data, training context data and/or associated training mapping rules. Furthermore, the database 250 can serve as an archive for one or more trained function(s) TF.

Figure 6:
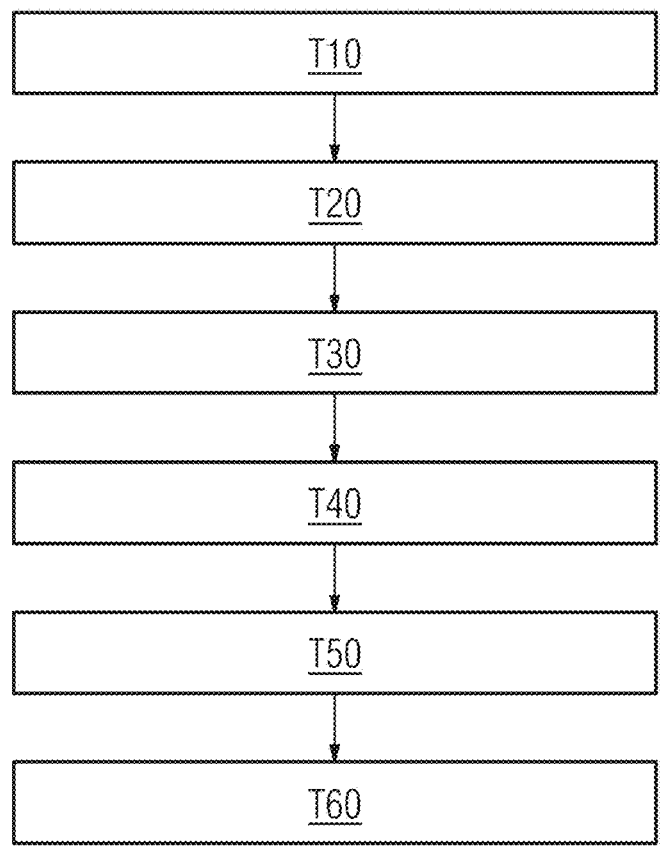
FIG. 6 shows a flowchart of a method for the provision of a trained function for improvement of a visualization image of a three-dimensional object according to one embodiment.

FIG. 6 represents a schematic flowchart of a method for the provision of a trained function TF for the provision of a mapping rule AV. The order of the method steps is limited by neither the represented sequence nor by the chosen numbering. The order of the steps can thus optionally be interchanged and individual steps can be omitted.

A first step T10 is directed toward providing a trained function TF. The processor 210 can be provided with the trained function TF by the database 250 via the interface 220. The trained function TF can be pre-trained already, in other words one or more parameter(s) of the trained function TF have already been adjusted by the described training method and/or a different training method. Alternatively, the one or more parameter(s) of the trained function can have not been adjusted by way of training data yet, in particular the one or more parameter(s) can be pre-allocated by a constant value and/or by a random value. In particular, all parameters of the trained function TF can have not been adjusted by way of training data yet, in particular all parameters can be pre-allocated by a constant value and/or by a random value.

A second step T20 is directed toward providing training input data. Since, in use, the trained function TF is to qualitatively provide mapping rules AV appropriate to the respective context data KD, suitable training input data is precisely training volume data and training context data.

Step T30 is directed toward providing training output data. The training output data is training mapping rules in this case. The training mapping rules constitute expedient mapping rules AV, which allow a suitable visualization.

In a next step T40, the training input data, training volume data and training context data, therefore, is input into the trained function TF. On this basis, the trained function TF calculates a mapping rule AV, which should enable a suitable visualization of the training volume data based on the training context data.

In a next step T50, the thus calculated mapping rule AV is compared with the associated training mapping rule. The trained function TF can then be adjusted in step T60 based upon this comparison. This can occur, for example, based upon a cost functional, which penalizes deviations of the calculated mapping rule AV from the associated training mapping rule. One or more parameter(s) of the trained function TF can then be adjusted in particular such that the cost functional is minimized, for example by way of a back propagation. The cost functional can be based in one embodiment on a pair-wise difference in control or visualization parameters of the calculated mapping rule AV and the associated training mapping rule, for example on the sum of the deviations squared. In order to minimize the cost functional the comparison is carried out for different pair-wise sets of calculated mapping rule AV and associated training mapping rule until a local minimum of the cost functional is achieved and the trained function TF is working satisfactorily.

Where it has not yet explicitly occurred but is expedient and within the meaning of the invention, individual example embodiments, individual partial aspects or features thereof can be combined with each other or replaced without departing from the scope of the present invention. Advantages of the invention described in relation to one example embodiment also apply without explicit mention, where transferable, to other example embodiments.

The following points are likewise part of the disclosure:
1. A computer-implemented method for the provision of a two-dimensional visualization image having a plurality of visualization pixels for the visualization of a three-dimensional object represented by volume data for a user, wherein the method has the following steps:
   providing the volume data;
   providing context data containing natural language and/or text in respect of the visualization of the three-dimensional object;
   determining a mapping rule based on the volume data and the context data, which mapping rule is capable of mapping the volume data onto a visualization image that is suitable when taking into account the context data;
   mapping the volume data onto the visualization pixels using the mapping rule for the creation of the visualization image; and
   providing the visualization image.
2. The method as claimed in 1, wherein the mapping of the volume data takes place by way of a volume rendering method, in particular using a ray casting method and/or path tracing method.
3. The method as claimed in one of the preceding points, wherein
   the context data comprises information about one or more preference(s) of the user in respect of the visualization of the volume data.
4. The method as claimed in one of the preceding points, wherein
   the context data has one or more electronic document(s) containing text relating to the object to be visualized, which documents comprise, in particular, one or more medical report(s) and/or medical guideline(s).
5. The method as claimed in 4, also with the following step
   retrieving one or more of the electronic document(s) from a database.
6. The method as claimed in one of the preceding points, wherein determining the mapping indication and/or the mapping rule takes place with a configuration algorithm, which comprises, in particular, a computer linguistics algorithm.
7. The method as claimed in 6, wherein
   the configuration algorithm has a trained function.
8. The method as claimed in one of the preceding points, wherein
   the volume data was generated by a medical imaging method and maps, in particular, one or more anatomy (anatomies) of a patient.
9. The method as claimed in one of the preceding points, wherein the step of mapping comprises:
   actuating an computing facility based on the mapping rule for the provision of the visualization image.

The example embodiments have been described for illustrative purposes. It will be obvious that the described features, steps and workflow may be varied in many ways. Such variations are not to be regarded as a departure from the scope of the present invention, and all such modifications as would be obvious to one skilled in the art are intended to be included within the scope of the following claims.

Of course, the embodiments of the method according to the invention and the imaging apparatus according to the invention described here should be understood as being example. Therefore, individual embodiments may be expanded by features of other embodiments. In particular, the sequence of the method steps of the method according to the invention should be understood as being example. The individual steps can also be performed in a different order or overlap partially or completely in terms of time.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for creating a two-dimensional visualization image including a plurality of visualization pixels for visualization of a three-dimensional object represented by volume data for a user, the method comprising:
   providing context data containing at least one of natural language or text for the visualization of the three-dimensional object;
   determining a mapping rule for the visualization of the three-dimensional object, the mapping rule determining a visualization of the three-dimensional object based on the volume data and the context data; and
   mapping the volume data onto the plurality of visualization pixels using the mapping rule, for creation of the two-dimensional visualization image.

2. The method of claim 1, wherein
   the volume data includes medical image data of a patient, and wherein the providing of the context data includes:
   retrieving patient data of the patient from a database,
   analyzing text information contained in the patient data using a text analysis algorithm, to produce a text analysis result, and
   providing the text analysis result as the context data.

3. The method of claim 2, wherein the determining of the mapping rule includes at least one of:
   establishing a suitable perspective for the two-dimensional visualization image;
   establishing a suitable scene illumination for the two-dimensional visualization image;
   establishing a suitable transfer function for calculation of visualization pixels of the two-dimensional visualization image from the volume data;
   establishing a suitable transparency of one or more regions of the volume data;
   establishing a suitable cutting plane through the volume data;
   establishing a suitable region of interest inside the volume data for representation in the two-dimensional visualization image; or
   establishing one or more suitable items of additional information for overlaying in the two-dimensional visualization image.

4. The method of claim 2, wherein the determining of the mapping rule includes:
   selecting a volume data set for visualization from the volume data based on the context data, wherein the two-dimensional visualization image is generated based upon the volume data set selected.

5. The method of claim 2, wherein
   the three-dimensional object includes a plurality of individual objects, represented in the volume data; and
   the determining of the mapping rule includes selection of one or more of the plurality of individual objects for representation in the two-dimensional visualization image based on the context data.

6. The method of claim 2, wherein the providing of the context data comprises:
   receiving an audio signal containing a speech input of the user via a detection facility;
   analyzing the speech input using a speech analysis algorithm to determine one or more voice commands of the user; and
   providing the one or more voice commands as the context data.

7. The method of claim 6, wherein
   the one or more voice commands are provided after providing the two-dimensional visualization image as the context data, the method further comprising:
   adjusting the mapping rule based on the context data, to create an adjusted mapping rule;
   mapping the volume data onto the visualization pixels using the adjusted mapping rule, to create an adjusted visualization image; and
   providing the adjusted visualization image.

8. The method of claim 2, wherein the determining of the mapping rule comprises:
   providing a trained function, the trained function being configured to match a visualization image to the context data; and
   determining the mapping rule by applying the trained function to the volume data and the context data.

9. A non-transitory computer program product storing a computer program, directly loadable into a storage device of a computing facility, including program segments to carry out the method of claim 2 when the program segments are run in the computing facility.

10. A non-transitory computer-readable storage medium storing program segments, readable and runnable by a computing facility, to carry out the method of claim 2 when the program segments are run in the computing facility.

11. The method of claim 1, wherein the determining of the mapping rule includes at least one of:
    establishing a suitable perspective for the two-dimensional visualization image;
    establishing a suitable scene illumination for the two-dimensional visualization image;
    establishing a suitable transfer function for calculation of visualization pixels of the two-dimensional visualization image from the volume data;
    establishing a suitable transparency of one or more regions of the volume data;
    establishing a suitable cutting plane through the volume data;
    establishing a suitable region of interest inside the volume data for representation in the two-dimensional visualization image; or
    establishing one or more suitable items of additional information for overlaying in the two-dimensional visualization image.

12. The method of claim 1, wherein the determining of the mapping rule includes:
    selecting a volume data set for visualization from the volume data based on the context data, wherein the two-dimensional visualization image is generated based upon the volume data set selected.

13. The method of claim 1, wherein
    the three-dimensional object includes a plurality of individual objects, represented in the volume data; and
    the determining of the mapping rule includes selection of one or more of the plurality of individual objects for representation in the two-dimensional visualization image based on the context data.

14. The method of claim 1, wherein the providing of the context data comprises:
    receiving an audio signal containing a speech input of the user via a detection facility;
    analyzing the speech input using a speech analysis algorithm to determine one or more voice commands of the user; and
    providing the one or more voice commands as the context data.

15. The method of claim 14, wherein
    the one or more voice commands are provided after providing the two-dimensional visualization image as the context data, the method further comprising:
    adjusting the mapping rule based on the context data, to create an adjusted mapping rule;
    mapping the volume data onto the visualization pixels using the adjusted mapping rule, to create an adjusted visualization image; and
    providing the adjusted visualization image.

16. The method of claim 1, wherein
    the context data includes one or more electronic documents containing text relating to the three-dimensional object to be visualized.

17. The method of claim 16, wherein the one or more electronic documents include at least one of one or more medical reports or one or more medical guidelines.

18. The method of claim 1, wherein the determining of the mapping rule comprises:
    providing a trained function, the trained function being configured to match a visualization image to the context data; and
    determining the mapping rule by applying the trained function to the volume data and the context data.

19. The method of claim 18, wherein the trained function has a neural network.

20. The method of claim 18, wherein the trained function has a convolutional neural network.

21. A non-transitory computer program product storing a computer program, directly loadable into a storage device of a computing facility, including program segments to carry out the method of claim 1 when the program segments are run in the computing facility.

22. A non-transitory computer-readable storage medium storing program segments, readable and runnable by a computing facility, to carry out the method of claim 1 when the program segments are run in the computing facility.

23. The method of claim 1, further comprising:
    providing the two-dimensional visualization image.

24. An apparatus for providing a two-dimensional visualization image including a plurality of visualization pixels for visualization of a three-dimensional object represented by volume data for a user, comprising:
    an interface, designed to receive the volume data and context data containing at least one of natural language or text relating to the visualization of the three-dimensional object;
    a computing facility, designed to determine a mapping rule for the visualization of the three-dimensional object, the mapping rule determining a visualization of the three-dimensional object based on the volume data and the context data; and
    a visualization module, designed to
        map the volume data onto the plurality of visualization pixels using the mapping rule, to create the two-dimensional visualization image; and
        provide the two-dimensional visualization image.

25. An apparatus for providing a two-dimensional visualization image including a plurality of visualization pixels for visualization of a three-dimensional object represented by volume data for a user, comprising:
    an interface to receive the volume data and context data containing at least one of natural language or text relating to the visualization of the three-dimensional object; and
    at least one processor to determine a mapping rule for the visualization of the three-dimensional object, the mapping rule determining a visualization of the three-dimensional object based on the volume data and the context data to map the volume data onto the plurality of visualization pixels using the mapping rule, to create the two-dimensional visualization image.

26. The apparatus of claim 25, further comprising a display to display the two-dimensional visualization image.

\* \* \* \* \*